United States Patent [19]

Hurter et al.

[11] 4,248,773
[45] Feb. 3, 1981

[54] ACETOACETAMIDE DIAZO DYESTUFFS

[75] Inventors: Rudolf Hurter, Basel; Alfred Fasciati, Bottmingen, both of Switzerland

[73] Assignee: Ciba-Geigy Corporation, Ardsley, N.Y.

[21] Appl. No.: 964,548

[22] Filed: Nov. 29, 1978

[30] Foreign Application Priority Data

Dec. 5, 1977 [LU] Luxembourg ............................ 78634

[51] Int. Cl.³ ............................................. C09B 45/30
[52] U.S. Cl. ................................. 260/148; 260/146 T; 260/146 R; 260/146 D; 260/156; 260/160; 260/163; 260/176; 260/193
[58] Field of Search ............... 260/148, 146 T, 146 R, 260/146 D, 156, 160, 163, 176, 193

[56] References Cited

U.S. PATENT DOCUMENTS

| | | | |
|---|---|---|---|
| 2,734,051 | 2/1956 | Iselin | 260/148 |
| 3,118,869 | 1/1964 | Berrie et al. | 260/146 T |
| 3,542,758 | 11/1970 | Hegar | 260/156 |
| 4,017,478 | 4/1977 | Dore | 260/146 T |
| 4,046,502 | 9/1977 | Moser et al. | 260/146 T |
| 4,118,381 | 10/1978 | Fuchs et al. | 260/148 |
| 4,118,382 | 10/1978 | Jäger et al. | 260/153 |

FOREIGN PATENT DOCUMENTS 1484732 9/1977 United Kingdom .

*Primary Examiner*—Arthur P. Demers
*Attorney, Agent, or Firm*—Edward McC. Roberts

[57] ABSTRACT

Novel compounds which have the formula I

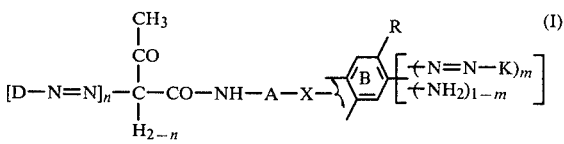

in which D is the residue of a diazo component, K is the residue of a coupling component, A is an unsubstituted or substituted 1,3- or 1,4-phenylene radical or an unsubstituted or substituted 1,4-naphthylene radical, X is an oxygen atom or sulphur atom, R is a group conferring solubility in water and n and m are each the numbers 0 or 1, with the proviso that if A is a 1,3-phenylene radical the symbol X is bonded in the p-position relative to the amino group or azo grouping of the ring B.

13 Claims, No Drawings

ACETOACETAMIDE DIAZO DYESTUFFS

The invention relates to novel compounds which in one of the possible tautomeric forms have the formula I

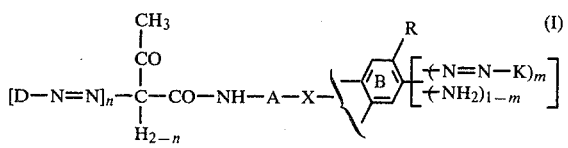

in which D is the residue of a diazo component, K is the residue of a coupling component, A is an unsubstituted or substituted 1,3- or 1,4-phenylene radical or an unsubstituted or substituted 1,4-naphthylene radical, X is a sulphur atom or preferably an oxygen atom, R is a group conferring solubility in water and n and m are each the numbers 0 or 1, with the proviso that if A is a 1,3-phenylene radical the symbol X is bonded in the p-position relative to the amino group or azo grouping of the ring B; and their preparation and the use of compounds of the formula I in which n and/or m is the number 1 as dyes for dyeing or printing natural or synthetic textile material, in particular material made of polyamide, wool, cotton and leather, and also the dyed or printed material.

A group R conferring solubility in water is, for example, a —SO$_3$H, —SO$_2$NH$_2$, —SO$_2$NHCH$_2$CH$_2$SO$_3$H, —SO$_2$N(CH$_3$)CH$_2$CH$_2$SO$_3$H, —PO$_3$H$_2$, —COOH or the

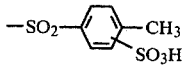

group; preferably, R is a —SO$_3$H group.

A diazo component D can be of any desired type. It is, for example, a diazo component of the aromatic or heterocyclic series. If D is the residue of an aromatic diazo component it can be, for example, the residue of aminobenzenes and aminonaphthalenes. If D is the residue of a heterocyclic diazo component, suitable residues are, in particular, the residues of 5-membered or 6-membered heterocyclic diazo components which contain, for example, N, O or S as the hetero-atom. Examples are the residues of aminopyrazoles, aminobenzpyrazoles, aminothiazoles and aminobenzthiazoles.

The residues D can also be further substituted by substituents customary in azo dyes, for example sulphonamide groups, which are unsubstituted or monosubstituted or disubstituted on the N atom; alkylamino groups; arylamino groups; alkyl groups; which are unsubstituted or substituted, for example by phenyl or halogen, for example the benzyl group or trifluoromethyl group; the nitro group, cyano group and hydroxyl group; alkoxy groups, such as the methoxy and ethoxy group; azo groups; halogen atoms, such as fluorine, chlorine or bromine; and also groups conferring solubility in water, of the type defined for R, and fibre-reactive groups.

Fibre-reactive groups are understood as meaning those which contain one or more detachable substituents which, when the compounds are applied to, for example, natural polyamide fibres, such as wool, are able to react with the NH groups of these fibres with the formation of covalent bonds. A large number of fibre-reactive groupings of this type is known from the literature.

Suitable fibre-reactive groups are, for example, those of the aliphatic series, such as acryloyl, mono-, di- or tri-chloro-acryloyl or -methacryolyl and mono-, di- or tri-bromo-acryloyl or -methacryloyl, such as —CO—CH=CH—Cl, —CO—CCl=CH$_2$, —CO—CH=CHBr, —COCBr=CH$_2$, —CO—C-Br—CHBr and —CO—CCl=CH—CH$_3$ and also —CO—CCl=CH—COOH, —CO—CH=C-Cl—COOH, β-chloropropionyl, 3-phenylsulphonylpropionyl, 3-methylsulphonylpropionyl, β-sulphatoethylaminosulphonyl, vinylsulphonyl, β-chloroethylsulphonyl, β-sulphatoethylsulphonyl, β-methylsulphonylethylsulphonyl, β-phenylsulphonylethylsulphonyl, 2-fluoro-2-chloro-3,3-difluorocyclobutane-1-carbonyl, 2,2,3,3-tetrafluorocyclobutane-1-carbonyl or -1-sulphonyl, β-(2,2,3,3-tetrafluorocyclobut-1-yl)-acryloyl and α- or β-alkyl- or -aryl-sulphonyl-acryloyl, such as α- or β-methylsulphonylacryloyl.

Reactive radicals especially suitable for polyamide and in particular for wool are: chloroacetyl, bromoacetyl, α,β-dichloro- or α,β-dibromo-propionyl, α-chloro- or α-bromo-acryloyl, 2,4-difluoro-5-chloropyrimid-6-yl, 2,4,6-trifluoropyrimid-5-yl, 2,4-dichloro-5-methylsulphonylpyrimid-6-yl, 2,4-difluoro-5-methylsulphonylpyrimid-6-yl, 2,4-difluorotriazin-6-yl and also fluorotriazinyl radicals of the formula

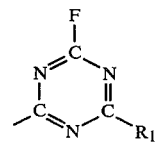

in which R$_1$ is a substituted or unsubstituted amino group or a free or etherified hydroxyl or thio group, for example the NH$_2$ group, an amino group monosubstituted or disubstituted by C$_1$–C$_4$-alkyl radicals, a C$_1$–C$_4$-alkoxy group, a C$_1$–C$_4$-alkylmercapto group, arylamino, especially phenylamino, or phenylamino substituted by methyl, methoxy, chlorine and, in particular, sulpho, and phenoxy, mono- or di-sulphophenoxy and the like.

Starting materials for introducing such triazine radicals are, for example, 2,4-difluoro- or 2,4-dichloro-6-aminotriazine, 2,4-difluoro- or 2,4-dichloro-6-methylaminotriazine, 2,4-difluoro- or 2,4-dichloro-6-ethylaminotriazine, 2,4-difluoro- or 2,4-dichloro-6-phenylaminotriazine, 2,4-difluoro- or 2,4-dichloro-6-(2', 3'- or 4'-sulphophenyl)-aminotriazine, 2,4-difluoro- or 2,4-dichloro-6-(2', 4'- or 3',4'- or 2',5'- or 4', 5'-disulphophenyl)-aminotriazine, 2,4-difluoro- or 2,4-dichloro-6-dimethylaminotriazine, 2,4-difluoro- or 2,4-dichloro-6-methoxytriazine, 2,4-difluoro- or 2,4-dichloro-6-(β-methoxyethoxy)-triazine, 2,4-difluoro- or 2,4-dichloro-6-methylmercaptotriazine and 2,4-difluoro- or 2,4-dichloro-6-phenylmercaptotriazine.

Particularly preferred reactive radicals are, in particular, the α-bromoacryloylamino group and the α,β-dibromopropionylamino group. The former can either be introduced with the aid of bromoacrylic acid chloride or obtained from the α,β-dibromopropionyl group by the elimination of hydrogen bromide. The same also applies analogously in the case of the α-chloroacryloylamino group. The 4,6-difluorotriazin-2-yl or the 4-fluoro-6-alkyl- or -6-aminotriazin-2-yl groups are also of interest.

Furthermore, the radical D can contain a metal-lisable group, in particular a hydroxyl group in the o-position relative to the azo bridge, and can contain a metal atom, such as Cu, Ni, Cr or Co, bonded as a complex, together with the enolised keto group of the acetoacetyl radical.

In preferred compounds of the formula I, D is an aromatic radical, in particular a phenyl radical, which is also further substituted, but especially a phenyl radical which is further monosubstituted or polysubstituted by alkyl having 1 to 4 carbon atoms, $SO_2H$, COOH, alkoxy having 1 to 4 carbon atoms, OH, halogen, $NO_2$, $SO_2NH_2$, COO-alkyl (1 to 4 carbon atoms), $SO_2$-Y, in which Y is alkyl having 1 to 4 carbon atoms or aryl, $SO_2NH(CH_2)_nNH_2$, in which n is an integer from 1 to 4, or a fibre-reactive radical.

Suitable radicals K are, for example, those of coupling components of the benzene, naphthalene and heterocyclic series, such as the hydroxybenzene, aminobenzene, aminonaphthalene, hydroxynaphthalene, aminohydroxynaphthalene, pyrazolone, aminopyrazole, acetoacetic acid arylamide and pyridine series, as are listed, for example, in Swiss Patent Specification No. 564,121. These radicals K can contain the substituents, fibre-reactive groups and groups capable of metal complex formation which are customary in azo dyes and have already been mentioned under the symbol D; the latter groups are then in the o-position relative to the azo bridge. If the radical K contains such metal complex-forming groups in the o-position relative to the azo bridge and if the formation of metal complex dyes on the radical K is desired, R is a —COOH group.

In compounds which are of particular interest, K is a naphthalene radical, especially an aminohydroxynaphthalenesulphonic acid radical. Examples of K are:

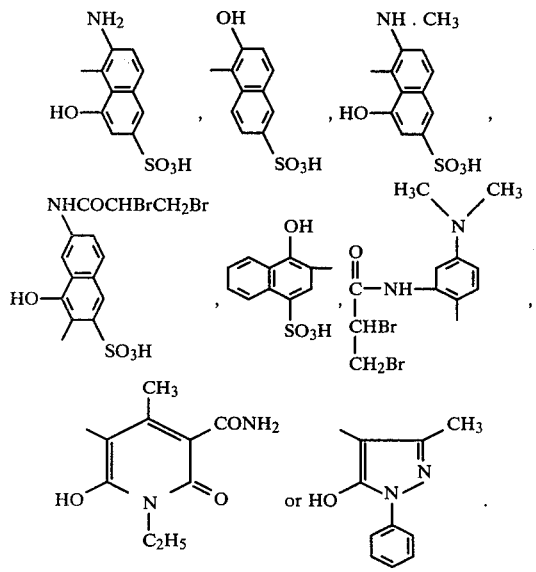

Substituents in the phenylene or naphthylene radical A are, in particular, halogen, such as fluorine, chlorine or bromine, lower alkyl groups, such as the methyl, ethyl or propyl group, lower alkoxy groups, such as the methoxy, ethoxy or n-butoxy group, and the $SO_3H$ group. In preferred compounds of the formula I, A is an unsubstituted 1,4-phenylene radical.

The compounds of the formula I in which n and m are each the number 0 are acetoacetyl compounds of the formula III

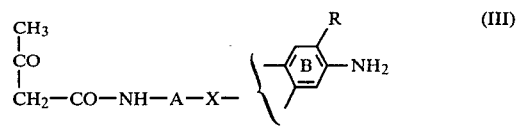

in which A, B, X and R are as defined under formula I. These compounds are used, in particular, as diazo components and coupling components for the preparation of monoazo and disazo dyes.

These acetoacetyl compounds of the formula III are obtained, for example, by reacting a compound of the formula

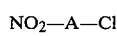

with a compound of the formula

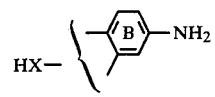

to give a compound of the formula

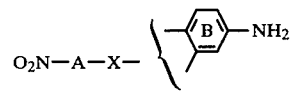

then reducing the $NO_2$ group to the $NH_2$ group and reacting the ether compound of the formula II

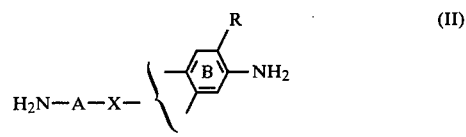

which is thus obtained and in which the symbols A, B, X and R are as defined under formula I, with diketene, the substituent R, if this is not already present in the starting material, being introduced prior to the reduction of the nitro group. The reaction with diketene is carried out, in particular, in aqueous solution at a pH value of about 4 to 7 and at a temperature of about 0° to 25° C.

The compounds of the formula I in which n in each case is the number 0 and the symbol m in each case is the number 1 are monoazo compounds of the formula IV

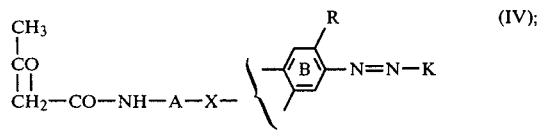

the compounds of the formula I in which n in each case is the number 1 and the symbol m in each case is the number 0 are monoazo compounds of the formula V

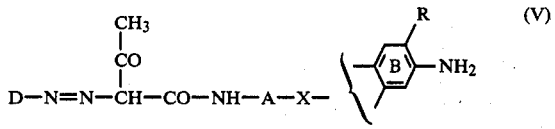

and the compounds of the formula I in which n and m are each the number 1 are disazo compounds of the formula Ia

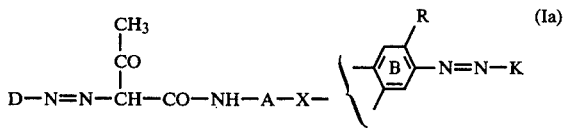

in which formulae the symbols D, A, B, X, R and K are as defined under formula I.

The novel monoazo and disazo compounds of the formulae IV, V and Ia are dyes and in particular those of the formula Ia are characterised by a very good affinity for the substrate, the dyeings obtained therewith having a high uptake, good fastness properties, such as wet fastness properties and fastness to light, and clear shades.

Disazo dyes of the formula Ib

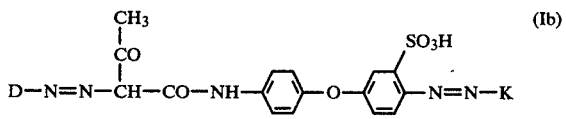

in which the symbols D and K are as defined under formula I, are of preferred interest because of their clear shades on polyamide.

The monoazo componds of the formula IV are obtained, for example, by diazotising an acetoacetyl compound of the formula III

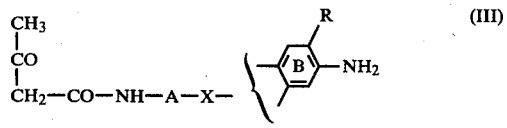

in which the symbols A, B, X and R are as defined under formula I, and coupling the diazo compound with a coupling component HK, which can be coupled in an acid pH range, preferably in a pH range of 3 to 6, in an aqueous medium at a temperature of about 0° to 20° C.

The monoazo compounds of the formula V are obtained, for example, by diazotising a diazo component D—NH$_2$ in a known manner and coupling the diazo compound with an acetoacetyl compound of the formula III.

The disazo compounds of the formula Ia, finally, are obtained, for example, by diazotising an acetoacetyl compound of the formula III

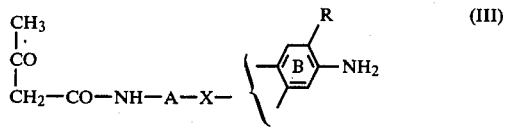

in which the symbols A, B, X and R are as defined under formula I, coupling the diazo compound with a coupling component HK which can be coupled in the acid pH range, to give a monoazo compound of the formula IV

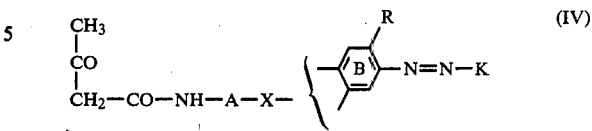

in which A, B, X, R and K are as defined under formula I, and then coupling a diazotised amine D—NH$_2$ with the monoazo compound of the formula IV.

A further possibility for the preparation of disazo compounds of the formula Ia comprises coupling a diazotised amine D—NH$_2$ with an acetoacetyl compound of the formula III and then diazotising the resulting monoazo compound of the formula V

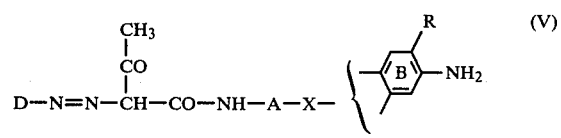

in which the symbols D, A, B, X and R are as defined, and coupling the resulting diazo compound with a coupling component HK which can be coupled in the weakly acid to alkaline pH range.

The coupling and diazotisation reactions are carried out in a known manner. cf., For example, Ullmanns Encyklopädie der technischen Chemie (Ullmann's Encyclopaedia of Industrial Chemistry), volume 5, (1954), page 783 et seq.

If the compounds of the formulae V and Ia also contain a metallisable group, such as a OH, COOH, or NH$_2$ group, in the radical D in the o-position relative to the azo bridge, these can, on the one hand, be converted with metal donors to 1:1 and 1:2 metal complex dyes or, on the other hand, can subsequently also be converted with pre-formed 1:1 metal complex dyes into an asymmetrical 1:2 metal complex dye. If compounds of the formulae IV and Ia also contain a metallisable group in the radical K in the o-position relative to the azo bridge and R is a COOH group, these compounds can also be converted with metal donors or with pre-formed 1:1 metal complex dyes to 1:1 and 1:2 metal complex dyes. It is thus possible to obtain metal complex compounds which contain the metal atom bonded to the radical D and/or K.

If the compounds of the formulae IV, V and Ia also contain amino groups which can be acylated, these can subsequently be reacted with a reactive compound which introduces an acyl radical, for example the acetyl or benzoyl radical, or a fibre-reactive radical. Reactants suitable for this purpose are, for example, those on which the said reactive groups are based, in general halides and in particular chlorides of the said components, and the condensation reaction is generally carried out in an aqueous or organic medium, advantageously in the presence of acid-binding agents.

If the compounds of the formulae IV, V and Ia also contain positions at which coupling can take place, these can be reacted with a further diazo component, by which means polyazo compounds are obtained. If, on the other hand, these compounds also contain amino groups which can be diazotised, these compounds can be reacted with a further coupling component, likewise to give polyazo compounds.

The coupling components HK, to which the acetoacetyl compounds of the formula III or the azo compounds of the formula V are coupled, are known. They are, for example, phenols, such as phenol, cresol and p-tert.-butylphenol; alkylanilines, such as diethylaniline and 3-dibromopropionylamino-1-dimethylaniline; naphthols, such as 2-naphthol and 5,8-dichloro-1-naphthol; aminonaphtholsulphonic acids and acyl- or alkylaminonaphtholsulphonic acids, such as 2- or 3-amino-8-naphthol-6-sulphonic acid, 1-amino-8-naphthol-3,6-disulphonic acid and 2-(N-methyl)- or -N-dibromopropionyl-amino-8-naphthol-6-sulphonic acid; aminonaphthalenesulphonic acids, such as 2-amino-naphthalene-6-sulphonic acid and 2-aminonaphthalene-5-sulphonic acid; naphtholsulphonic acids, such as 1-naphthol-4-sulphonic acid or 2-naphthol-6-sulphonic acid; naphthalene derivatives, such as 2-phenylnaphthylamine; pyrazolones and pyrazolimines, such as a 1-aryl-3-methylpyrazol-5-one and a 1-aryl-3-methyl-5-aminopyrazole, "aryl" signifying, in particular, phenyl and also phenyl which can be substituted by methyl, ethyl, halogen, especially chlorine, methoxy, ethoxy and sulpho; and pyridones, such as 1-ethyl-4-methyl-3-carbamoyl- or -3-cyano- or 3-sulphomethyl-6-hydroxy-pyrid-2-one.

The diazo components D—NH$_2$, which are coupled with the azo compounds of the formula IV or with the acetoacetyl compounds of the formula III, are also known. Examples of such diazo components are: 1-amino-2-methylbenzene, 1-amino-2-hydroxy-5-chlorobenzene, 1-amino-2-hydroxy-5-nitrobenzene, 1-amino-2-hydroxybenzene-5-sulphonic acid amide, 1-amino-3-α,β-dibromopropionylaminobenzene-6-sulphonic acid, 1-amino-4-α,β-dibromopropionylaminobenzene-6-sulphonic acid, 1-amino-4-α,β-dibromopropionylaminobenzene and 2-aminobenzoic acid.

The novel compounds of the formula I in which n and/or m is 1 are used as dyes for dyeing and printing very diverse natural and synthetic textile materials, in any made-up form, such as fibres, filaments and fabrics, and also leather. If the dyes are acid dyes which can contain fibre-reactive groups, these are used to dye and print, in particular, natural and synthetic polyamide materials, and also cellulose materials. If the dyes are metal complex dyes, these are used in particular for dyeing or printing wool, synthetic polyamide and leather. The dyeings are carried out in a known manner by a continuous process or by the exhaustion process.

The dyes are distinguished by a good affinity for the fibre, especially by good build-up and uptake and at the same time have generally good fastness properties, especially good fastness to light, good wet fastness properties, such as fastness to washing, fastness to milling, fastness to hot water, fastness to alkali, fastness to acid, fastness to perspiration and fastness to damp heat, and also good fastness to rubbing. They level well and give intense, brilliant dyeings.

The following examples illustrate the invention without restricting it thereto. The temperatures are in degrees centigrade. The dyes or intermediates can be in the form of the free acid or in the form of an alkali metal salt thereof, for example the Na, K or Li salt, or the NH$_4$ salt, or in the form of an inner salt.

EXAMPLE 1

(A) Acetoacetylation 84 g of 4,4'-diaminodiphenyl ether-3-sulphonic acid are stirred in 400 ml of water and the pH of the mixture is adjusted to 7 with sodium hydroxide solution at room temperature and the mixture is warmed briefly to form a solution. 25.2 ml of diketene are added dropwise in the course of about 1 hour, with ice-cooling. The temperature is allowed to rise to room temperature and after 2 hours the product is precipitated with sodium chloride, filtered off and dried in vacuo at 60° to 70°.

110.8 g of the acetoacetyl compound of the formula

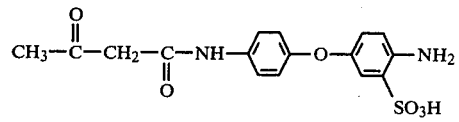

are obtained.

(B) Diazotisation and coupling of the acetoacetyl compound

(a) Diazotisation:

36.4 g of the acetoacetyl compound according to (A) are dissolved in 300 ml of hot water at pH 7. After adding 25 ml of 4 N sodium nitrite, the solution is added dropwise to a mixture of 300 g of ice and 25 ml of concentrated hydrochloric acid. By means of external cooling, the temperature of the reaction mixture is kept below +2°. After stirring further for a short time, a small amount of excess nitrite is destroyed with sulphamic acid.

(b) Coupling:

23.9 g of gamma acid (2-amino-8-hydroxy-naphthalene-6-sulphonic acid) are dissolved in 100 ml of water at room temperature with sodium hydroxide solution at a pH value of 7 to 7.5. This solution is added dropwise to a suspension of the diazonium salt according to (Ba). The pH value is kept below 4 using 4 N sodium acetate. After the coupling reaction has ended, the pH is adjusted to 5 with sodium hydroxide solution and the product is precipitated by adding sodium chloride. After filtering off and drying at 50° to 60° in vacuo, 57.2 g of the monoazo compound of the formula

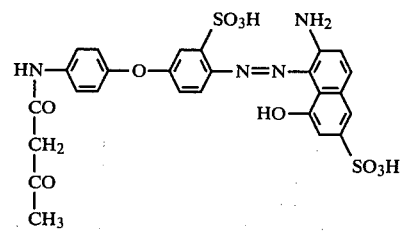

are obtained.

(C) Preparation of the disazo compound

(a) Diazotisation:

2.55 g of o-chloroaniline are dissolved in 50 ml of water with the addition of 5 ml of concentrated hydrochloric acid, at room temperature. The diazotisation reaction is carried out at 0° to 3° with 5 ml of 4 N sodium nitrite. After a short time, a small amount of excess nitrite is destroyed with sulphamic acid.

(b) Coupling:

12.28 g of the monoazo compound according to (Bb) are dissolved in 200 ml of water at room temperature at about pH 7. The solution is cooled to 5° and the solution of the diazonium salt of o-chloroaniline, prepared according to (Ca), is then allowed to run in slowly dropwise. At the same time, the pH value is maintained at 6 to 7 using 4 N sodium acetate. After the coupling reaction has ended, the resulting suspension is warmed until it is in a good form and is filtered. The dye is washed with 5% aqueous sodium chloride solution and dried in vacuo at 50° to 60°.

14.84 g of the red disazo compound of the formula

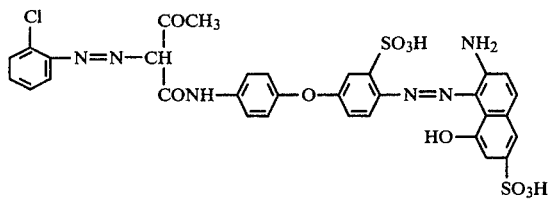

are obtained.

When the indicated procedure is repeated except that equivalent amounts of the diazo components D—NH$_2$ listed in Table I below are used in place of the 2.55 g of o-chloroaniline, red disazo compounds are again obtained and these are distinguished by very pure colour shades on polyamide and wool and a good build-up and very good fastness properties.

TABLE I

| Example No. | D—NH$_2$ |
|---|---|
| 2 | (2-methylaniline) |
| 3 | (2-methoxy-4-chloroaniline) |
| 4 | (methyl 2-aminobenzoate) |
| 5 | (2-aminophenyl phenyl sulfone) |
| 6 | (4-amino-phenol, NH$_2$ para to OH) |
| 7 | SO$_2$NHCH$_2$CH$_2$NH$_2$ (2-aminobenzenesulfonamide-ethylenediamine) |

When the same procedure is repeated except that equimolecular amounts of the ether compounds listed in column 2 of Table II are used in place of the 84 g of 4,4'-diamino-diphenyl ether-3-sulphonic acid according to Example 1 (A), the acetoacetyl compounds listed in column 3 are obtained and these can be reacted further in accordance with the instructions of Examples 1 to 7 to give monoazo and disazo compounds.

TABLE II

| 1 Example | 2 Ether compound | 3 Acetoacetyl compound |
|---|---|---|
| 8 | 3-amino-phenyl 2-amino-4-sulfophenyl ether | corresponding acetoacetylamino derivative |
| 9 | 4-amino-phenyl 2-amino-5-sulfophenyl ether | corresponding acetoacetylamino derivative |
| 10 | 4-amino-2-chloro-phenyl 2-amino-5-sulfophenyl ether | corresponding acetoacetylamino derivative |

TABLE II-continued

| 1 Example | 2 Ether compound | 3 Acetoacetyl compound |
|---|---|---|
| 11 |  |  |

EXAMPLE 12

Diazotisation 10.75 g of 1-amino-4-α,β-dibromopropionylaminobenzene in the form of the hydrochloride are dissolved in 300 ml of hot water and the solution is then cooled again to below room temperature. A suspension is obtained by the dropwise addition of 18 ml of an approximately 30% solution of naphthalenesulphonic acid and 7.5 ml of 4 N sodium nitrite are allowed to run dropwise into the suspension. The reaction mass is stirred a little longer and a small amount of excess nitrite is destroyed with sulphamic acid.

Coupling to give the monoazo dye 10.92 g of the acetoacetyl compound of the formula

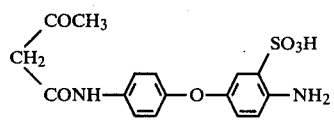

are dissolved in 150 ml of water at room temperature at a pH value of 7 and the solution is cooled to 2°. After adding 15 ml of 4 N sodium acetate, the suspension of the diazonium salt prepared above is added in portions. The coupling reaction is brought to completion by raising the pH value to 7 with sodium hydroxide solution. The compound which is filtered off is washed with sodium chloride solution and dried at 50° to 60°.

The monoazo compound of the formula

is obtained.

Diazotisation of the monoazo compound 6.97 g of the monoazo compound are taken up in 100 ml of water at room temperature and, after adding 2.5 ml of concentrated hydrochloric acid, the mixture is cooled to 2°. Diazotisation is effected by the dropwise addition of 10 ml of 1 N sodium nitrite.

Coupling to give the disazo compound 4.53 g of N-dibromopropionyl-gamma acid are dissolved in 100 ml of water at room temperature and pH 7. The diazo compound prepared above, of the monoazo compound is added in the cold and the pH value is kept constant at about the neutral point using sodium hydroxide solution. After the coupling reaction has ended, the mixture is filtered and the product is washed with sodium chloride solution and dried at 50° to 60°.

The disazo compound of the formula

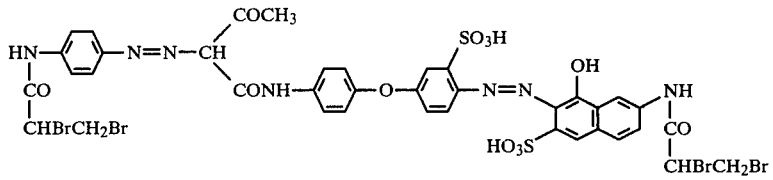

is obtained.

This compound acts as a reactive dye, for example for dyeing wool and polyamide. The resulting red dyeings have good fastness properties.

EXAMPLES 13 TO 16

When the procedure followed is analogous to the instructions of Example 1, except that equivalent amounts of the diazo components D—NH$_2$ listed in column 2 of Table III below are used in place of the 2.55 g of o-chloroaniline according to (Ca) and in other respects the procedure is as indicated, disazo compounds containing a fibre-reactive group in the radical D are obtained.

TABLE III

| 1 Example | 2 D—NH$_2$ |
|---|---|
| 13 | SO$_3$H, NH$_2$, NHCOCHBrCH$_2$Br (benzene ring) |
| 14 | NH$_2$, NHCOCHBrCH$_2$Br (benzene ring) |

TABLE III-continued

| 1 Example | 2 D—NH$_2$ |
|---|---|
| 15 | SO$_2$NHCH$_2$CH$_2$NHCOCHBrCH$_2$Br, —NH$_2$ (on benzene ring) |
| 16 | benzene with NH$_2$ and NH-linked triazine (N, N, N; Cl; NH—CH$_2$CH$_2$OH) |

These red fibre-reactive disazo compounds are very suitable as dyes for dyeing polyamide, wool and cotton and have good fastness properties, clear shades and a good build-up.

EXAMPLES 17 TO 20

When the procedure followed is analogous to the instructions of Example 1 except that equivalent amounts of diazo components of the amines D—NH$_2$ listed in column 2 of Table IV below are used in place of the o-chloroaniline according to (Ca), red metallisable disazo compounds are obtained which can be reacted with Co salts to give symmetrical 1:2 Co metal complex compounds. On polyamide and wool, the metal complex compounds give yellowish-tinged red dyeings which have good fastness properties.

TABLE IV

| 1 Example | 2 D—NH$_2$ |
|---|---|
| 17 | OH, NH$_2$ on benzene |
| 18 | OH, NH$_2$, NO$_2$ on benzene |
| 19 | OH, NH$_2$, Cl on benzene |
| 20 | OH, NH$_2$, SO$_2$NH$_2$ on benzene |

EXAMPLE 21

10 g of a wool piece are dyed for 30 to 90 minutes at a temperature of 98° in an aqueous liquor containing, based on the weight of fibre, 4 percent by weight of ammonium sulphate, 1.5 percent by weight of 80% acetic acid, 1 percent by weight of Albegal B and 2 percent by weight of the dye according to Example 13. The dyebath is then cooled to 80° and neutralised by adding dyebath is then cooled to 80° and neutralised by adding 2.5 percent by weight of 25% aqueous ammonia and the dyeing is finished for 15 minutes at this temperature. The dyed wool piece is then removed and washed and dried in the customary manner.

A red-coloured wool piece is obtained which has a clear shade and good overall fastness properties.

EXAMPLE 22

7.79 g of the disazo dye according to Example 18 are dissolved at 80° in 250 ml of water with the addition of 10 ml of 2 N sodium hydroxide solution. 5 ml of 1 M cobalt sulphate are added and the mixture is stirred for a further ½ hour at 78° to 82°. After adding sodium chloride, the dye which has precipitated is filtered off warm, washed with sodium chloride solution and dried at 50° to 60°. 8.3 g of the symmetrical 1:2 cobalt complex of the formula

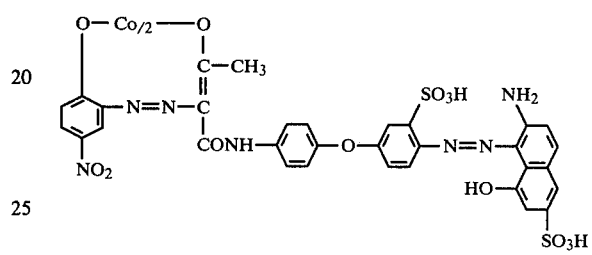

are obtained.

100 parts of garment suede leather (dry weight) are drummed for 2 hours at 50° in a solution of 1,000 parts of water and 2 parts of 24% ammonia and then dyed for 1 hour at 60° in a solution of 1,000 parts of water, 2 parts of 24% ammonia and 6 parts of the above cobalt complex dye. A solution of 40 parts of water and 4 parts of 85% formic acid are then added and dyeing is continued for a further 30 minutes. The leather is then rinsed well and, if desired, also treated for 30 minutes at 50° with 2 parts of a dicyandiamide/formaldehyde condensation product. A red-coloured suede leather with good fastness to light is obtained.

Other suede leathers and glove leathers can be dyed in the same way.

EXAMPLE 23

3 parts of the dye obtained according to Example 16 are dissolved in 100 parts of water with the addition of 1 part of sodium m-nitrobenzenesulphonate. A cotton fabric is impregnated with the resulting solution so that its weight increases by 75%, and is then dried.

The fabric is then impregnated with a solution, at 20°, which contains, per liter, 30 ml of an aqueous 30% sodium hydroxide solution and 250 g of sodium chloride and squeezed off to 75% increase in weight and the dyeing is steamed for 60 seconds at 100° to 103°, rinsed, soaked for a quarter of an hour in a 0.1% boiling solution of a nonionic detergent, rinsed and dried. A red-coloured cotton fabric is obtained.

EXAMPLE 24

10 g of Helanca tricot are dyed in 500 ml of an aqueous liquor which contains 1 g/l of monosodium phosphate and the pH of which has been adjusted to 6 with disodium phosphate. The proportion of dye according to Example 2 is 2%, based on the weight of fibre. The dyeing time at a temperature of 98° is 30 to 90 minutes. The dyed piece of Helanca is then removed and washed and dried in the customary manner.

A red-coloured piece of Helanca is obtained which has a clear shade and very good overall fastness properties.

What is claimed is:

1. A compound of the formula

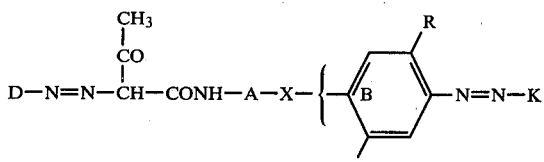

wherein
D is a residue of a diazo component,
K is a residue of a coupling component,
A is 1,3-phenylene, 1,4-phenylene, chloro-1,4-phenylene, or 1,4-naphthylene,
X is an oxygen atom or a sulfur atom,
R is an acidic water solubilizing group, provided that when A is 1,3-phenylene, X is para to the azo group of ring B.

2. A compound of claim 1, wherein R is the —$SO_3H$, —$SO_2NH_2$, —$PO_3H_2$, —COOH or the

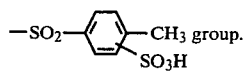

group.

3. A compound of claim 2, wherein R is the $SO_3H$ group.

4. A compound of claim 1, wherein X is an oxygen atom.

5. A compound of claim 1, wherein A is 1,4-phenylene.

6. A compound of claim 1, wherein D is a phenyl radical which is further monosubstituted or polysubstituted by alkyl having 1 to 4 carbon atoms, $SO_3H$, COOH, alkoxy having 1 to 4 carbon atoms, OH, halogen, $NO_2$, $SO_2NH_2$, COO-alkyl (1 to 4 carbon atoms), $SO_2$—Y, in which Y is alkyl having 1 to 4 carbon atoms or aryl, $SO_2NH(CH_2)_nNH_2$, in which n is an integer from 1 to 4, or a fibre-reactive radical.

7. A compound of claim 1, wherein K is an aminohydroxy-naphthalenesulphonic acid radical.

8. A compound of claim 1, wherein K is one of the following radicals:

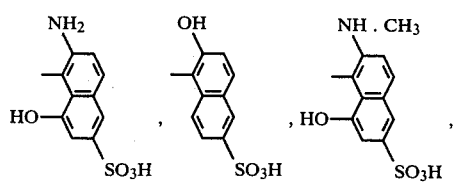

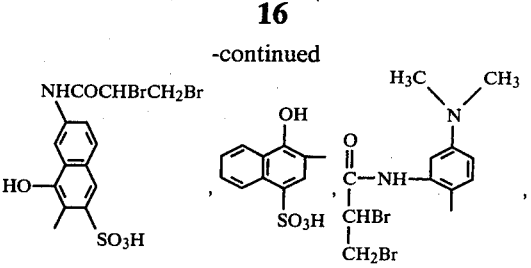

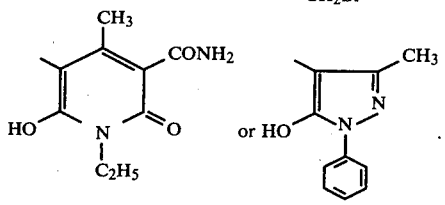

9. A compound of claim 1 the formula

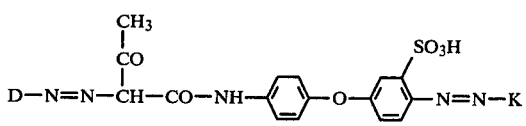

10. A disazo dye of the formula

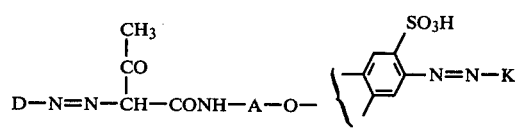

in which D is a phenyl radical which is monosubstituted or polysubstituted by $SO_2NH_2$, $NO_2$, $SO_3H$, Cl, $CH_3$, $OCH_3$, $COOCH_3$, $SO_2C_6H_5$, OH, $SO_2NHCH_2CH_2NH_2$, $SO_2NHCH_2CH_2NH$-$COCHBrCH_2Br$, $NHCOCHBrCH_2Br$ or

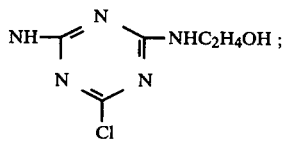

A is an unsubstituted 1,3-phenylene or 1,4-naphthylene radical, or a 1,4-phenylene radical which is unsubstituted or substituted by chlorine, and K is the radical

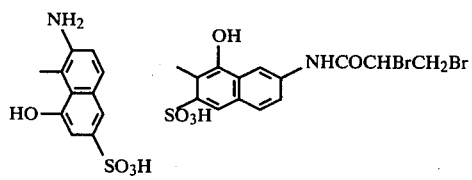

11. A compound of claim 1, wherein K is an alkylaniline residue.

12. A compound of claim 11, wherein K is the diethylaniline residue.

13. A disazo dye of claim 10, wherein D is metallized with cobalt.

* * * * *